(12) United States Patent
Goy et al.

(10) Patent No.: US 11,109,932 B2
(45) Date of Patent: *Sep. 7, 2021

(54) SURGICAL DRAPE INCLUDING A LAYER TO PROTECT THE OPERATOR FROM SCATTERED RADIATION DURING CARDIOLOGIC AND RADIOLOGIC INVASIVE PROCEDURES

(71) Applicants: Jean-Jacques Francois Goy, Cuarny (CH); Doris Luana Goy, Cuarny (CH); Christophe Jean-Michel Augereau, Prez-vers-Noreaz (CH)

(72) Inventors: Jean-Jacques Francois Goy, Cuarny (CH); Doris Luana Goy, Cuarny (CH); Christophe Jean-Michel Augereau, Prez-vers-Noreaz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/789,511

(22) Filed: Feb. 13, 2020

(65) Prior Publication Data

US 2020/0179073 A1 Jun. 11, 2020

Related U.S. Application Data

(63) Continuation of application No. 15/812,684, filed on Nov. 14, 2017, now Pat. No. 10,675,111.

(Continued)

(51) Int. Cl.
*A61B 46/00* (2016.01)
*A61B 90/00* (2016.01)
(Continued)

(52) U.S. Cl.
CPC .............. *A61B 46/40* (2016.02); *A61B 6/107* (2013.01); *A61B 46/00* (2016.02); *A61B 90/04* (2016.02); *G21F 3/00* (2013.01); *G21F 1/08* (2013.01)

(58) Field of Classification Search
CPC ......... A61B 46/00; A61B 46/10; A61B 46/13; A61B 46/17; A61B 46/20; A61B 46/23;
(Continued)

(56) References Cited

U.S. PATENT DOCUMENTS 4,670,658 A   6/1987  Meyers et al.
8,079,365 B2  12/2011 Block et al.
(Continued)

OTHER PUBLICATIONS

Abbott, Controlling Radiation Exposure in Interventional Cardiology, Circ Cardiovasc Interv. 2014;7:425-428.
(Continued)

*Primary Examiner* — Camtu T Nguyen
(74) *Attorney, Agent, or Firm* — Arrigo, Lee, Guttman & Mouta-Bellum

(57) ABSTRACT

Invasive cardiology and radiology are widespread procedures that involve the use of X-ray radiations for imaging. During these procedures, the operators are exposed to a variable dose of radiation. It is shown that these professionals are among the most exposed to ionizing radiations. New studies have shown that brain cancers can be linked to these exposures. As these exposures are harmful to health, maximum protection is required to protect the patient and the staff. The current invention provides an improved protective shield to fully protect the staff in cardiologic, angiologic, and radiologic procedures. The present invention relates to a modified surgical drape that include a layer that absorbs the X-rays scattered from the patient's body during invasive angiology procedures.

19 Claims, 6 Drawing Sheets

Related U.S. Application Data

(60) Provisional application No. 62/474,651, filed on Mar. 22, 2017.

(51) Int. Cl.
*A61B 6/10* (2006.01)
*G21F 3/00* (2006.01)
*G21F 1/08* (2006.01)

(58) Field of Classification Search
CPC ......... A61B 46/27; A61B 46/30; A61B 46/40; A61B 2046/201; A61B 2046/205; A61B 2046/234; A61B 2090/0436; A61B 2090/0454; A61B 2090/0481; A61B 90/04; A61B 6/107; G21F 3/00; G21F 3/02; G21F 3/025; G21F 3/03; G21F 1/08
See application file for complete search history.

(56) References Cited

U.S. PATENT DOCUMENTS

| | | | |
|---|---|---|---|
| 8,350,241 B2 | 1/2013 | Bustamante Grant et al. | |
| 9,192,344 B2 | 11/2015 | Cadwalader et al. | |
| 9,416,485 B2 | 8/2016 | Moore et al. | |
| 9,487,893 B2 | 11/2016 | Moore et al. | |
| 2002/0109107 A1* | 8/2002 | Goldstein | G21F 3/00 250/505.1 |
| 2002/0148980 A1 | 10/2002 | Cadwalader et al. | |
| 2006/0076522 A1 | 4/2006 | Goldstein et al. | |
| 2006/0108548 A1 | 5/2006 | Cadwalader et al. | |
| 2007/0113859 A1 | 5/2007 | Allen et al. | |
| 2008/0035159 A1 | 2/2008 | Perez-Cruet et al. | |
| 2008/0164425 A1 | 7/2008 | Cadwalader et al. | |
| 2011/0165373 A1 | 7/2011 | Khandkar et al. | |
| 2012/0132217 A1 | 5/2012 | Rees et al. | |
| 2014/0029720 A1* | 1/2014 | Osherov | A61B 6/4441 378/62 |
| 2016/0100892 A1 | 4/2016 | Wu et al. | |

OTHER PUBLICATIONS

Andreassi et al., Occupational Health Risks in Cardiac Catheterization Laboratory Workers, Circ Cardiovasc Interv. 2016;9:e003273.
Bruschi et al., Staff Dose Reduction During Coronary Angiographies Procedures Using Radio-Absorbing Surgical Drapes, Abstracts/ Physica Medica 32 (2016) e74, B.248.
Cardinal Health, Surgical Drapes and Ancillary Products, 2016.
Chambers et al., Radiation Safety Program for the Cardiac Catheterization Laboratory, Catheterization and Cardiovascular Interventions 00:000-000 (2011).
Cohen et al., A Novel Radiation Protective Drape Reduces Radiation Exposure During Fluoroscopy-Guided Electrophysiologic Procedures, NASPE Abstracts & Programs, May 14-17, 2003.
Domnici et al., Operator exposure to x-ray in left and right radial access during percutaneous coronary procedures: OPERA randomised study, Heart 2013;99:480-484.
Ertel et al., Radiation Dose Reduction during Radial Cardiac Catheterization: Evaluation of a Dedicated Radial Angiography Absorption Shielding Drape, ISRN Cardiology vol. 2012, Article ID 769167, 5 pages.
Germano et al., Electrophysiology: A Novel Radiation Protection Drape Reduces Radiation Exposure during Fluroscopy-Guided Electrophysiology Procedures, J Invasive Cardiol. 2005;17(9):469-472.
Kallinikou et al., Radiation Exposure of the Operator During Coronary Interventions (from the RADIO Study) Am J Cardiol 2016;118:188-194.
Kern et al., Do You Know Your Radiation Dose During Your Cath? Cath Lab Digest vol. 19—Issue 6—Jun. 2011 (/issue/6793).
King et al., Using a Sterile Disposable Protective Surgical Drape for Reduction of Radiation Exposure to Interventionalists, AJR 2002;178:153-157.
Lange et al., Randomized Comparison of Operator Radiation Exposure During Coronary Angiography and Intervention by Radial or Femoral Approach, Catheterization and Cardiovascular Interventions 67:12-16 (2006).
Meisinger et al., Radiation Protection for the Fluoroscopy Operator and Staff, AJR 2016; 207:745-754.
Murphy et al., Efficacy of the RADPAD Protective Drape During Real World Complex Percutaneous Coronary Intervention Procedures, Am J Cardiol 2011;108:1408-1410.
Partridge, Radiation in the Cardiac Catheter Laboratory, Heart 2005;91:1615-16.
Rouguin et al., Brain tumours among interventional cardiologists: a cause for alarm? EuroIntervention vol. 7, No. 9, Jan. 20, 2012.
Saunamaki et al., Radiation protection in the cardiac catheterization laboratory: special focus on the role of the operator, Interv. Cardiol. (2010) 2(5), 667-672.
Vano et al., Radiation exposure to cardiologists: how it could be reduced, Heart 2003;89:1123-1124.
3M Health Care, Surgical Drape Packs, 2017.
European Patent Office, European Serach Report for EP17207275, dated Mar. 5, 2018.

* cited by examiner

FIG. 2A

| Procedure ID | With or without the device | Procedure duration (minutes) | Access Radial L:0 Radial R:1 Femoral R:2 | Imaging time (sec) | Cumulative air kerma | Number of images acquired | Cummulative Dose μSv Operator | Peak Frequency Dose μSv/h Operator | Mean Frequency Dose μSv/h Operator | Cummulative Dose μSv Assistant | Peak Frequency Dose μSv/h Assistant | Mean Frequency Dose μSv/h Assistant |
|---|---|---|---|---|---|---|---|---|---|---|---|---|
| C14-1868 | without | 0:19 | 0 | 549.00 | 759 | 996 | 29 | 4440 | 87 | 2 | 167 | 6 |
| C14-1869 | without | 0:24 | 0 | 188.00 | 466 | 599 | 5 | 906 | 11 | 3 | 1570 | 7 |
| C14-1872 | without | 0:07 | 0 | 154.00 | 169 | 511 | 7 | 1550 | 50 | 1 | 270 | 7 |
| C14-1873 | without | 0:04 | 0 | 79.00 | 314 | 371 | 10 | 5450 | 113 | 3 | 1600 | 49 |
| C14-1874 | without | 0:05 | 0 | 152.00 | 142 | 371 | 13 | 2820 | 110 | 0 | 145 | 4 |
| C14-1896 | without | 0:07 | 0 | 190.00 | 572 | 715 | 5 | 2560 | 39 | 0 | 258 | 4 |
| C14-1900 | without | 0:09 | 0 | 227.00 | 371 | 616 | 8 | 971 | 51 | 3 | 921 | 22 |
| C14-1901 | without | 0:04 | 0 | 220.00 | 302 | 568 | 5 | 2340 | 49 | 1 | 219 | 7 |
| C14-1903 | without | 0:20 | 0 | 433.00 | 470 | 798 | 19 | 3870 | 60 | 10 | 2970 | 30 |
| C14-1904 | without | 0:18 | 0 | 447.00 | 775 | 922 | 38 | 2080 | 124 | 2 | 364 | 5 |
| C14-1905 | without | 0:43 | 0 | 938.00 | 1289 | 842 | 13 | 1050 | 18 | 4 | 396 | 6 |
| C15-0170 | without | 0:09 | 2 | 90.00 | 61 | 329 | 4 | 392 | 28 | 0 | 147 | 3 |
| C15-0174 | without | 0:11 | 2 | 182.00 | 142 | 393 | 4 | 1250 | 21 | 2 | 341 | 11 |
| C15-0175 | without | 0:20 | 2 | 382.00 | 334 | 623 | 5 | 887 | 16 | 3 | 593 | 10 |
| C15-0346 | without | 0:26 | 2 | 520.00 | 661 | 1114 | 71 | 5720 | 163 | 7 | 377 | 16 |
| C15-0094 | without | 0:08 | 2 | 221.00 | 214 | 525 | 7 | 0:00 | 0:00 | 1 | 555 | 9 |
| C15-0045 | without | 0:15 | 2 | 925.00 | 595 | 209 | 36 | 5010 | 139 | 4 | 233 | 17 |
| Average | without | | | 346.9 | 449.2 | 617.8 | 16.4 | 2500.4 | 66.4 | 2.7 | 654.5 | 12.5 |
| C16-1127 | with | 0:32 | 2 | 317.00 | 274 | 678 | 2 | 2 | 2 | 0 | 0 | 0 |
| C16-1432 | with | ? | 1 | 142.00 | 414 | 693 | 0 | 190 | 23 | 4 | 1770 | 91 |
| C16-1433 | with | 0:13 | 1 | 79 | 186 | 366 | 0 | 0 | 0 | 0 | 0 | 0 |
| C16-1434 | with | 0:17 | 2 | 294.00 | 739 | 488 | 5 | 1790 | 17 | 0 | 0 | 0 |

FIG. 2B

| | | | | | | | | |
|---|---|---|---|---|---|---|---|---|
| C16-1435 | with | 0:05 | 2 | 127 | 566 | 0 | 24 | 1 | 0 | 0 |
| Average | with | | | 191.8 | 367.4 | 558.2 | 1.4 | 401.2 | 8.6 | 0.8 | 354 | 18.2 |
| | | | | | | | | | | | |
| Right Radial 1 | without | 0:06 | 1 | 103.00 | 586 | 473 | 23 | 9040 | 231 | not measured | not measured | not measured |
| Right Radial 2 | without | 0:39 | 1 | 763.00 | 1581 | 1103 | 43 | 5190 | 66 | | | |
| Right Radial 3 | without | 0:06 | 1 | 161.00 | 213 | 539 | 12 | 2960 | 116 | | | |
| Right Radial 4 | without | 0:06 | 1 | 109.00 | 113 | 446 | 5 | 941 | 54 | | | |
| Right Radial 5 | without | 0:51 | 1 | 452.00 | 261 | 526 | 9 | 1070 | 23 | | | |
| Right Radial 6 | without | 0:16 | 1 | 289.00 | 1083 | 700 | 11 | 2360 | 41 | | | |
| Right Radial 7 | without | 0:07 | 1 | 168.00 | 385 | 382 | 19 | 3180 | 170 | | | |
| Right Radial 8 | without | 0:11 | 1 | 195.00 | 344 | 879 | 12 | 1310 | 62 | | | |
| Right Radial 9 | without | 0:07 | 1 | 173.00 | 744 | 528 | 30 | 6740 | 261 | | | |
| Right Radial 10 | without | 0:14 | 1 | 505.00 | 877 | 522 | 31 | 7480 | 134 | | | |
| Right Radial 11 | without | 0:06 | 1 | 117.00 | 556 | 446 | 7 | 807 | 66 | | | |
| Right Radial 12 | without | 0:05 | 1 | 86.00 | 429 | 422 | 14 | 3640 | 163 | | | |
| Right Radial 13 | without | 0:05 | 1 | 96.00 | 512 | 413 | 13 | 5250 | 158 | | | |
| Right Radial 14 | without | 0:06 | 1 | 176.00 | 413 | 511 | 10 | 1470 | 88 | | | |
| Right Radial 15 | without | 0:05 | 1 | 94.00 | 379 | 316 | 8 | 2610 | 96 | | | |
| Right Radial 16 | without | 0:54 | 1 | ##### | 1244 | 922 | 17 | 1560 | 19 | | | |
| Right Radial 17 | without | 0:06 | 1 | 131.00 | 540 | 676 | 8 | 1720 | 72 | | | |
| Average | | | | 293.5 | 603.5 | 576.7 | 16.0 | 3372.2 | 107.1 | | | |

SURGICAL DRAPE INCLUDING A LAYER TO PROTECT THE OPERATOR FROM SCATTERED RADIATION DURING CARDIOLOGIC AND RADIOLOGIC INVASIVE PROCEDURES

CROSS REFERENCE TO RELATED APPLICATIONS

This application is a continuation of U.S. application Ser. No. 15/812,684, filed Nov. 14, 2017, which claims the benefit of U.S. provisional Application 62/474,651, filed Mar. 22, 2017, both of which are herein incorporated by reference in their entirety.

DESCRIPTION OF THE BACKGROUND ART

In many medical procedures, X-ray live imaging of the patient is necessary to guide the operator. However, X-rays are well known to be carcinogenic and to induce various health damage. It is thus always desirable to minimize the exposure to X-rays, both for the patient and the operator. The X-ray dose delivered to the patient, for a specific type of X-ray machine, depends directly on the imaging time. It is the responsibility of the operator to minimize the exposure time by avoiding unnecessary imaging. As far as the operator is concerned, the problem is similar. There is obviously no need for the operator to be exposed and all measures are usually taken to reduce the X-rays dose on the operator and other members of the staff. Moreover, the staff is exposed to X-rays on a daily basis as opposed to the patient, who undergoes only sporadic exposure. Protection of the staff is thus regarded as a very important issue by health authorities.

In angioplasty procedures, X-ray imaging is typically performed with a machine that has an X-ray source on one side of the patient and a detector on the opposite side. The whole machinery can rotate and image the patient's body under various angles. When no patient is present between the source and the detector, most of the X-rays travel directly from the source to the detector. When the patient is present, part of the X-ray radiation still reaches the detector, where its intensity is recorded to compose the image delivered to the operator. However, in that case, a significant part (typically as high as 30%) of the X-rays are scattered by the patient's body and form what is commonly referred to as the secondary radiation. The secondary radiation is diffuse and may travel in all possible directions from the patient's body thus irradiating the surrounding staff.

Up to now, various devices have been used to screen the secondary radiation. These devices include rigid screens that can be slid over the patient, but also soft pads of various size and shape to be placed manually by the operator where required.

Radiation shielding placed directly on the patient can decrease scatter. One such shield is a small bismuth-based disposable shield (RADPAD, Worldwide Innovations and Technologies). When placed between the patient and the operator and outside of the primary beam, this shield can reduce operator doses by 44%. Meisinger et al., AJR:207, October 2016, 745-754. Small, lightweight disposable cloths with a 0.1-mm lead equivalency decreased scattered radiation to one-ninth to one-fifth of the original value with an increase overall patient entrance exposure rate of 30-40%, owing to compensating radiation beam adjustments made by the automatic exposure control. Id. Proper positioning is key, because placement of this or any high attenuation object in the path of the primary beam can markedly increase radiation to the patient through automatic exposure control. Id.

As the radiation is diffuse, the protective gear has to cover all possible radiation angles. In practice, this has been difficult to achieve, partly because the imaging machinery needs to move around the patient, and the operator needs to have unobstructed access to different parts of the patient. The above-mentioned free-standing protecting pads can be placed directly on the patient to fill the gaps. However, since the operator cannot see the X-ray secondary radiation that still leaks through the patchy barrier composed of those different devices, the operator does not always know how to place the free-standing pads or even which one to use. For example, one particular gap that has been spotted in recent studies is the region of the patient arm close to the operator. Kallinikou et al., Am J Cardiol. 118(2):1 88-94, 2016. A large amount of diffuse radiation leaks through the gap, and it is practically difficult to cover it due to its proximity to the edge of the table. Presently, a large radio-protective sheet for cardiology and angiology surgery does not exist on the market.

Thus, there is a need in the art for better radio-protection for the protection of operators. The invention fulfills this need.

BRIEF SUMMARY OF THE INVENTION

The invention encompasses a sterile surgical drape comprising an integrated radio-protective layer. Preferably, the surgical drape is at least 130 cm in width and at least 130 cm in length. Most preferably, the integrated radio-protective layer is at least 130 cm in width and at least 60 cm in length.

In some embodiments, the integrated radio-protective layer, and the associated surgical drape, has at least one or two precut hole(s) that can be opened, and preferably closed afterwards, to allow access to the patient.

In some embodiments, the integrated radio-protective layer comprises at least one precut hole of at least 5 cm in diameter.

In some embodiments, the integrated radio-protective layer comprises at least two precut holes of at least 5 cm in diameter and separated by between 90 cm and 110 cm.

In some embodiments, the integrated radio-protective layer comprises at least two precut holes of at least 5 cm in diameter and separated by between 20 cm and 50 cm.

In some embodiments, the integrated radio-protective layer comprises at least two precut holes of at least 5 cm in diameter and separated by between 50 cm and 90 cm.

In some embodiments, the integrated radio-protective layer comprises at least two precut holes of at least 5 cm in diameter and separated by between 90 cm and 110 cm and at least two precut holes of at least 5 cm in diameter and separated by between 20 cm and 50 cm.

In some embodiments, the precut holes are between 5 cm and 15 cm in diameter.

In some embodiments, the sterile surgical drape further comprises at least two rectangular extensions of the precut holes of at least 5 cm by 10 cm.

In some embodiments, the integrated radio-protective layer comprises a hole of at least 30 cm×30 cm, preferably between 30 cm×30 cm and 40 cm×50 cm.

In some embodiments, the surgical drape is at least 190 cm in length. In some embodiments, the surgical drape is at least 250 cm in length.

In some embodiments, surgical drape is at least 200 cm in width.

In some embodiments, the integrated radio-protective layer has at least 0.25 mm lead equivalence at 70 kVp.

BRIEF DESCRIPTION OF THE DRAWINGS

The drawings herein illustrate the present invention, wherein:

FIG. 2A-B: Results of surgical drapes comprising an integrated radio-protective layer versus RADPADs in various coronary interventions.

DETAILED DESCRIPTION OF THE INVENTION

Figure 1A:
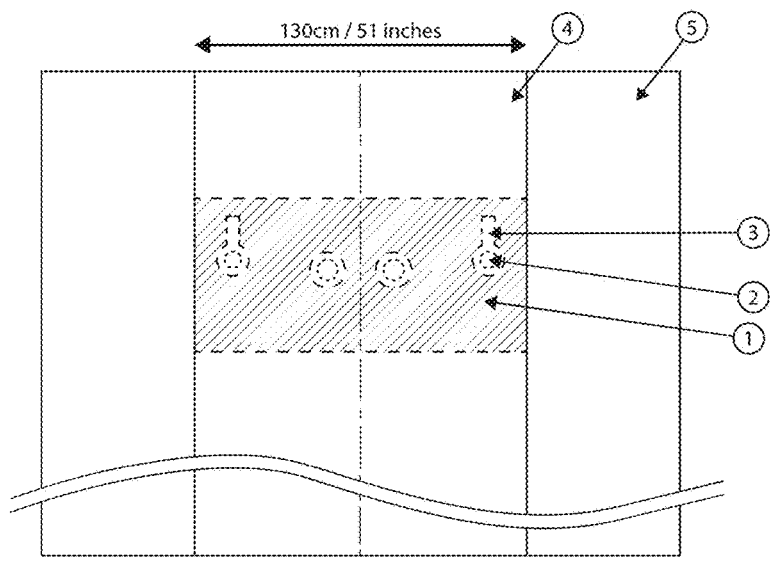
FIG. 1A-C: Illustrative embodiment of surgical drape typically used in angioplasty operations. A) Schematic of part of a surgical drape for use in angioplasty operations. 1) Hatched area indicates the region covered by the radio-protecting layer. 2) The dotted lines indicate the pre-cut access ports in the drape. 3) Areas of the drape free of radio-protection for imaging a longer portion of the artery. 4) Conventional surgical drape. 5) lateral plastic flaps (included in a conventional surgical drape). (B) Photograph of a surgical drape area corresponding to the portion shown in A. (B): Photograph of a complete surgical drape.

The present invention specifically matches the need of minimizing the X-ray diffuse radiation from the patient's body. The invention relates to a new type of surgical drape that includes a radio-protecting layer. This layer stops the radiation in places that were usually uncovered, either because there was no suitable device to stop it, or because the operator was not aware of the radiation emanating from that location. Because of its large coverage, the drape offers an almost full protection for the operator and the assistant.

The drape of the invention has two components. The first is a common sterile surgical drape. The second is the radio-protection layer—a radiation absorbing sheet integrated into the surgical drape. The radio-protection layer is not present over the full extent of the drape, but only in the strategic regions. The radio-protection layer is also sterile.

The common sterile surgical drape provides surgical light sterile protection. In some embodiments, it can cover the whole patient and the table of examination, which aim is sterility protection. The radio-protection layer is able to stop all or most of scattered radiation from the patient.

In various embodiments, the radiation absorbing sheet has pre-cut holes that can be opened to allow access to the patient and allow the operator to choose the convenient site for the intervention. For example, the holes can allow access to the left arm (LA), right arm (RA), left femoral (LF) or right femoral (RF) approach, before initiating the procedure by simple opening of the pre-cut hole. In this way, the invention provides a Specific Electromagnetic operator combined sterile Protection drape Against scattered Radiation (SEPAR).

Integrating the radio-protection layer within the drape offers numerous advantages. The invention offers larger and more reliable coverage since the operator does not always know where to effectively place smaller forms of radio-protection. Smaller forms of radio-protection can disturb the procedure since it may have to be moved, as opposed to the surgical drape, which is present anyway. The smaller forms of radio-protection can slide by accident, particularly when located on the side of the patient.

It was surprisingly found that this new radio-protective device could reduce operator exposure by 90% compared to RADPADs and completely eliminate operator and assistant exposure in many cases. It was unexpected that use of the present invention would result in such a large increase in radio-protection for the operator and assistant, since it was previously assumed that the smaller forms of radio-protection were adequate in most circumstances. The impressive degree of increased protection offered by the integrated radio-protection layer was surprising and was not expected.

Surgical Drape

The invention encompasses a surgical drape comprising an integrated radio-protective layer. The surgical drape is sterile. The radio-protection layer does not move independently from the surgical drape.

Surgical drapes are well-known in the art and can be made of many materials (e.g., U.S. Pat. Nos. 9,487,893, 9,416,485, and 8,079,365, which are hereby incorporated by reference). Surgical drapes are available commercially, for examples from Cardinal Health, Arc Royal, or Kimberly-Clark.

In various embodiments, the surgical drape has a width (i.e. from side to side of the patient) of at least 100, 110, 120, 130, 140, 150, 160, 170, 180, 190, 200, 210, 220, 230, 240, or 250 cm.

In various embodiments, the surgical drape has a length (i.e. from head to feet of the patient) of at least 100, 110, 120, 130, 140, 150, 160, 170, 180, 190, 200, 210, 220, 230, 240, 250, 260, 280, 300, 320, 340, 360, 380, or 400 cm. Each and every combination of width and height is specifically contemplated.

Most preferably, the surgical drape has a width of at least 130 cm and a length of at least 130 cm.

Preferably, the drape is of sufficient width to fully cover the patient from side to side, including the arms of the patient. Preferably, the drape is of sufficient length to fully cover the patient from head, or neck, to feet.

Radio-Protection Layer

Within the context of this invention, a radio-protective layer is a layer of an X-ray absorbing compound that prevents the passage of at least ½ of the X-ray radiation at 70 kVp.

In various embodiments, the radio-protection layer has a width (i.e. from side to side of the patient) of at least 100, 110, 120, 130, 140, 150, 160, 170, 180, 190, or 200 cm. Preferably, the radio-protection layer is of sufficient width to fully cover the patient from side to side, including the arms of the patient.

In various embodiments, the radio-protection layer has a length (i.e. from head to feet of the patient) of at least 40, 50, 60, 70, 80, 90, 100, 110, or 120 cm. Each and every combination of width and height is specifically contemplated. In addition, each and every combination of size of radio-protection layer with a larger size of surgical drape is specifically contemplated Most preferably, the radio-protection layer has a width of at least 130 cm and a length of at least 60 cm or 80 cm or 130 cm.

The radio-protection layer can be integrated into the surgical drape within existing layers of the surgical drape or as an additional layer. Preferably, the surgical drape retains its absorbency and imperviousness to liquids.

The radio-protection layer can be made of any X-ray absorbing compound. Preferably, the X-ray absorbing compound is essentially free of lead. In some embodiments, the X-ray absorbing compound is a metal powder for example bismuth oxide [$Bi_2O_3$], antimony, gadolinium oxide [$Gd_2O_3$], or barium sulfate [$BaSO$]). In one embodiment, the X-ray absorbing compound is a BaSO—$Bi_2O_3$ composite. The X-ray absorbing compound can comprise blend of metals and minerals including tungsten, tin, antimony, cerium oxide and trace metals other than lead.

Preferred compounds can be found in radio-protective materials sold as KIARMOR (Infab Corp.), SORBX (AngioSystems, Inc.), RADPAD (Worldwide Innovations & Technologies, Inc.), and WIROMA (Lanz-Ankiler AG) devices.

In various embodiments, the integrated radio-protective layer has at least 0.05, 0.1, 0.2, 0.25, 0.3, 0.35, 0.4, or 0.5 mm lead equivalence at 70 kVp. Preferably, the integrated radio-protective layer has between 0.20, 0.25, or 0.30 and 0.25, 0.30, or 0.35 mm lead equivalence at 70 kVp. More preferably, the integrated radio-protective layer has between 0.20 and 0.30, most preferably, 0.25, mm lead equivalence at 70 kVp.

Preferably, the integrated radio-protective layer provides a 10-fold increase in protection of the operator and/or assistant as compared to a 37 cm×42 cm RADPAD, determined using the procedures in the Examples or a comparable procedure.

Precut Holes

In various embodiments, the radio-protection layer, and the associated surgical drape, comprises at least one, two, three, or four precut hole(s) that allows access to the patient. In some embodiments, the holes are permanently placed and do not need to be opened. In other embodiments, precut holes can be can be opened to allow access to the patient.

In some embodiments, the precut holes can be closed after allowing access to the patient. In some embodiments, a flap may be employed to allow opening and closing of the precut holes.

In various embodiments, the integrated radio-protective layer comprises at least one precut circular hole of at least 5, 6, 7, 8, 9, 10, 11, 12, 13, 14, or 15 cm in diameter. In various embodiments, the integrated radio-protective layer comprises at least two precut circular holes of at least 5, 6, 7, 8, 9, 10, 11, 12, 13, 14, or 15 cm in diameter. Preferably, the holes are separated by between 20 cm and 110 cm as measured from the center to center of the holes.

In various embodiments, the integrated radio-protective layer comprises at least two precut circular holes of at least 5, 6, 7, 8, 9, 10, 11, 12, 13, 14, or 15 cm in diameter and separated by between 90 cm and 110 cm as measured from the center to center of the holes. In various embodiments, the precut holes are square or rectangular and of at least 5, 6, 7, 8, 9, 10, 11, 12, 13, 14, or 15 cm in width and length.

In various embodiments, the integrated radio-protective layer comprises at least two precut holes of at least 5, 6, 7, 8, 9, 10, 11, 12, 13, 14, or 15 cm in diameter and separated by between 20 cm and 50 cm as measured from the center to center of the holes. In various embodiments, the precut holes are square or rectangular and of at least 5, 6, 7, 8, 9, 10, 11, 12, 13, 14, or 15 cm in width and length.

In various embodiments, the integrated radio-protective layer comprises at least two precut circular holes of at least 5, 6, 7, 8, 9, 10, 11, 12, 13, 14, or 15 cm in diameter and separated by between 50 cm and 90 cm as measured from the center to center of the holes. In various embodiments, the precut holes are square or rectangular and of at least 5, 6, 7, 8, 9, 10, 11, 12, 13, 14, or 15 cm in width and length.

In various embodiments, the integrated radio-protective layer comprises (1) at least two precut holes of at least 5, 6, 7, 8, 9, 10, 11, 12, 13, 14, or 15 cm in diameter and separated by between 90 cm and 110 cm, as measured from center to center, and (2) at least two precut holes of at least 5, 6, 7, 8, 9, 10, 11, 12, 13, 14, or 15 cm in diameter and separated by between 20 cm and 50 cm, as measured from center to center. In various embodiments, the integrated radio-protective layer further comprises at least two rectangular extensions of the precut holes. Preferably, the rectangular extensions are of at least 5, 6, 7, 8, 9, 10, 11, 12, 13, 14, or 15 cm by 5, 6, 7, 8, 9, 10, 11, 12, 13, 14, or 15 cm. Each and every combination of numbers and sizes of holes and extensions is specifically contemplated.

Figure 4:
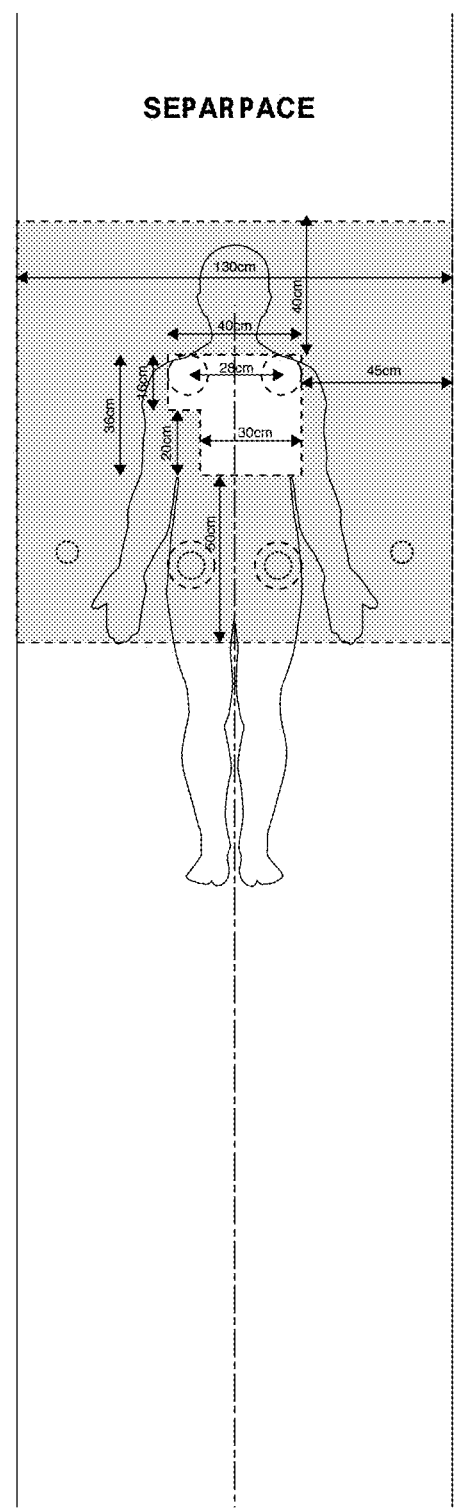
FIG. 4: An embodiment (SEPARPACE) showing exemplary measurements of the radio-protective layer of a device of the invention. Possible positions and sizes for precut rectangles are shown. The size of the sterile drape is not drawn to scale—it need only be larger than the radio-protective layer and at least 100 cm×100 cm.
Figure 5:
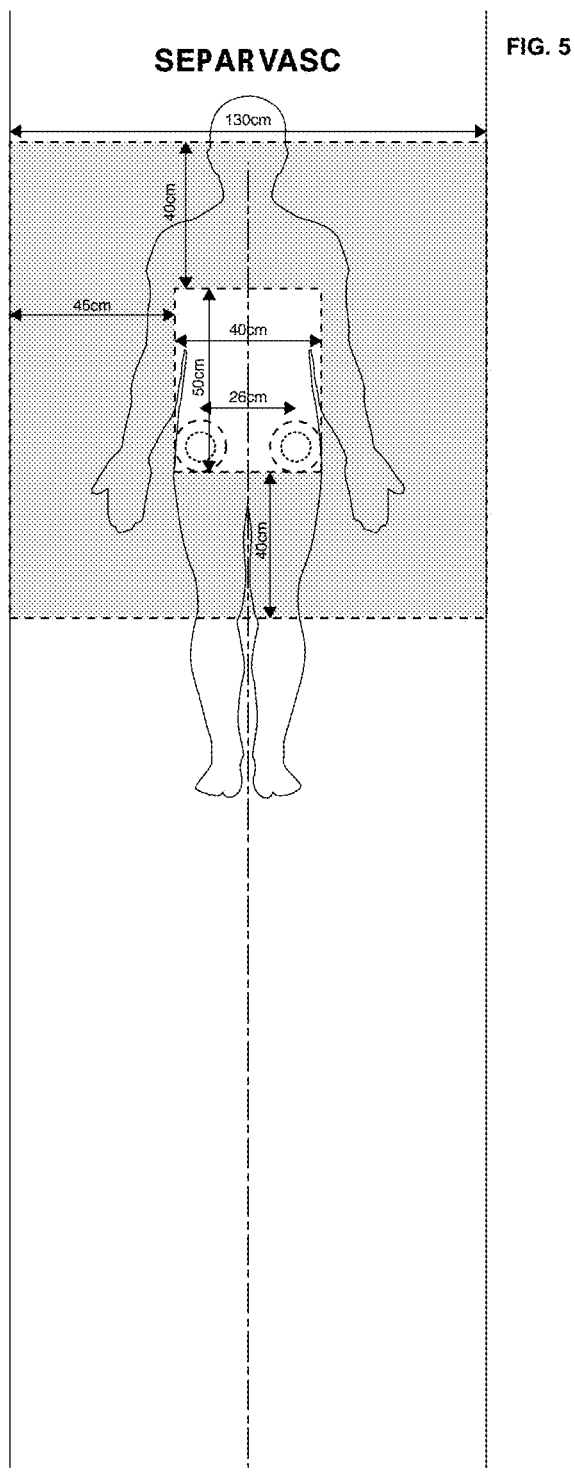
FIG. 5: An embodiment (SEPARVASC) showing exemplary measurements of the radio-protective layer of a device of the invention. The possible position and size for a precut rectangle are shown. The size of the sterile drape is not drawn to scale—it need only be larger than the radio-protective layer and at least 100 cm×100 cm.

In some embodiments, the integrated radio-protective layer comprises a precut square or rectangular hole of at least 30 cm×30 cm. The hole can provide access for surgical intervention and/or imaging. The precut hole is preferably between 30 cm×30 cm and 50 cm×50 cm, more preferably between 30 cm×30 cm and 30 cm×40 cm, 30 cm×50 cm, or 40 cm×50 cm. Examples are shown in FIG. 4 and FIG. 5. The area of the hole is less than 50% of the area of the radio-protective layer, preferably, less than 25%, 20%, 15%, 10% or 5% of the area of the radio-protective layer.

In some embodiments, the integrated radio-protective layer comprises (1) a precut hole of at least 30 cm×30 cm and (2) an additional connected hole of at least 10×10 cm. The additional connected hole is preferably between 10 cm×10 cm and 20 cm×30 cm, more preferably between 10 cm×15 cm and 15 cm×15 cm, 15 cm×20 cm, or 20 cm×20 cm. An example is shown in FIG. 4. The sum of the area of the hole and the an additional connected hole is less than 50% of the area of the radio-protective layer, preferably, less than 25%, 20%, 15%, 10% or 5% of the area of the radio-protective layer.

Methods and Uses

The invention encompasses the use of the drape of the invention for shielding an operator and/or assistant from radiation during a surgical procedure. Thus, the invention encompasses the drape of the invention for shielding an operator and/or assistant from radiation during a surgical procedure.

The invention further encompasses methods of using the drape of the invention for shielding an operator and/or assistant from radiation during a surgical procedure. In various embodiments, the drape of the invention is spread over the patient to provide shielding. The operator and assistant are protected from radiation when the patient is irradiated.

Figure 3:
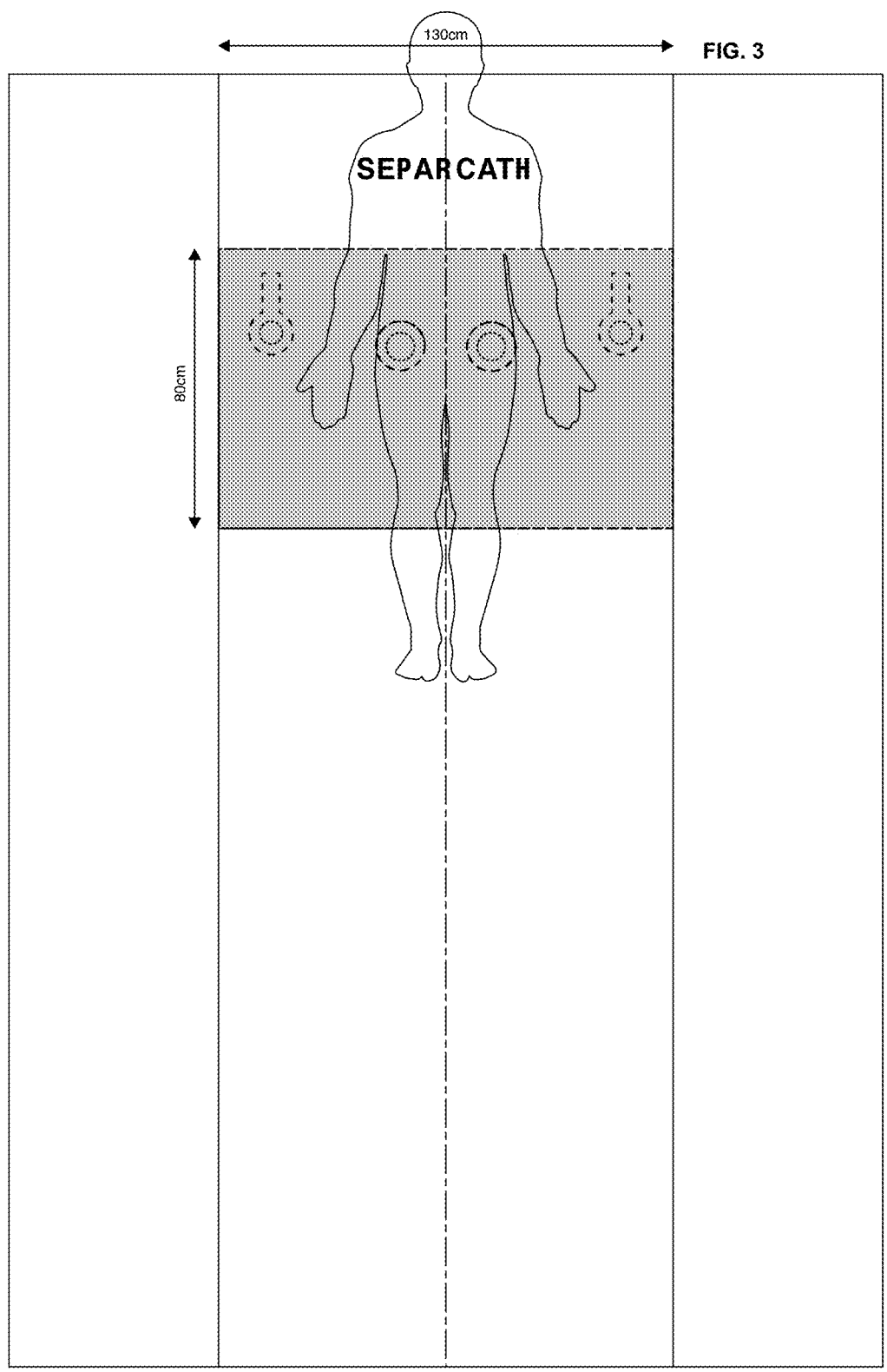
FIG. 3: An embodiment (SEPARCATH) showing exemplary measurements of the radio-protective layer of a device of the invention. Possible positions and sizes for precut access ports are shown. The size of the sterile drape is not drawn to scale—it need only be larger than the radio-protective layer and at least 100 cm×100 cm.

In one embodiment, the invention encompasses the use of the drape of the invention for catheterization procedures. A suitable device for performing such a procedure is shown in FIG. 3 (SEPARCATH).

In one embodiment, the invention encompasses the use of the drape of the invention for pacemaker and/or defibrillator procedures. A suitable device for performing such a procedure is shown in FIG. 4 (SEPARPACE).

In one embodiment, the invention encompasses the use of the drape of the invention for vascular procedures. A suitable device for performing such a procedure is shown in FIG. 5 (SEPARVASC).

EXAMPLES

Figure 1B:
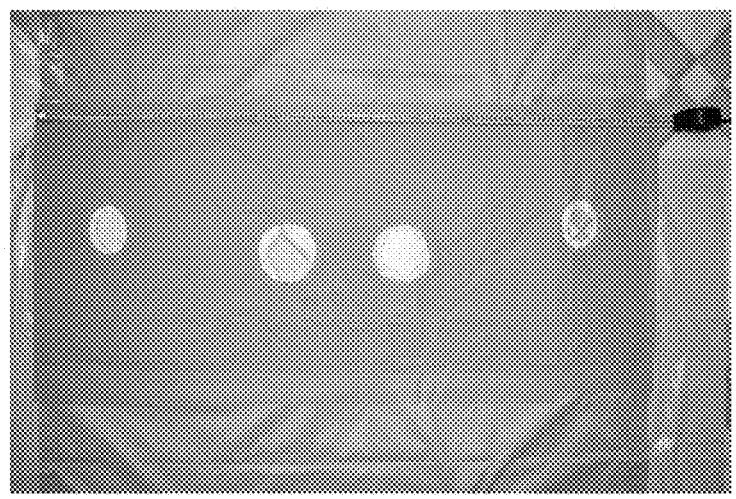
Figure 1C:
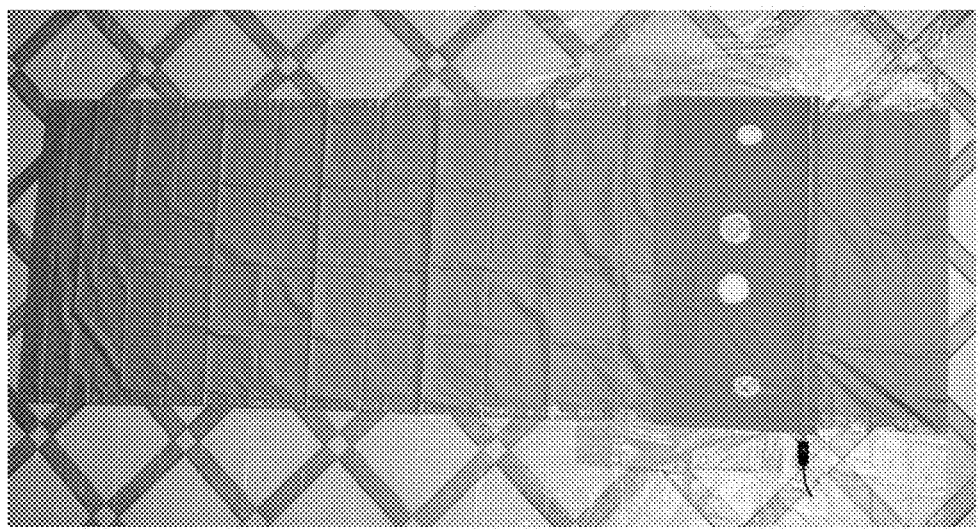

Sterile Surgical Drape Comprising an Integrated Radio-Protective Layer 0.25 mm lead equivalent X-LIGHT WIROMA radio-protective film was cut to an appropriate shape and taped onto a regular commercially available surgical drape. Openings in the radio-protective film were made to face the openings in the surgical drape to generate surgical drapes as shown in FIG. 1. The drape of FIG. 1 has a radio-protective layer of approximately 130 cm by 60 cm=7800 $cm^2$. The drapes were compared to RADPADS (37 cm×42 cm=1554 $cm^2$) placed over the access site in each procedure to reduce scatter radiation in various coronary interventions using left radial access, right radial access, or right femoral access. The surgical drapes were effective in eliminating movement of the radio-protection during the procedure.

The exposure to the operator and assistant were measured by the use of dosimeters (DoseAware; Philips Healthcare, Best, The Netherlands) positioned on the sternum, outside the lead apron. The dosimeters are silicon-based semiconductor detectors with a dose-response between 1 mSv and 10 Sv, in steps of 1 mSv (calibrated in ambient equivalent dose Hp(10)) and a temporal resolution of 1 second. The following parameters were recorded for each procedure: (1) operator CD through the use of dedicated readout software (DoseView), measured by the individual dosimeters; (2) FT; (3) number of cine angiograms (NC); and (4) the DAP-normalized CD defined as the dose (mSv) received by the operator with each Gycm2 applied to the patient (known as the exposure factor) has been advocated and applied to our study as it isolates differences in patient radiation among the 3 vascular access sites. The results are shown in FIGS. 2A-C.

Using RADPADS, the average cumulative dose of the operator was approximately 16 µSv, with a range of 4-43 µSv. Unexpectedly, using the sterile surgical drapes comprising an integrated radio-protective layer, the average cumulative dose of the operator was reduced to approximately 1.4 µSv, with a range of 0-5 µSv. Surprisingly, in three of the five procedures conducted with the drape of the invention, no cumulative dose of the operator was detected at all. Thus, the drape of the invention nearly eliminated operator exposure, causing a more than 10-fold reduction in exposure compared to the RADPADS. The drape of the invention also reduced assistant exposure. Surprisingly, in four of the five procedures conducted with the drape of the invention, no cumulative dose of the assistant was detected at all.

Thus, it was surprising to find that the drape of the invention nearly eliminated operator and assistant exposure during these procedures.

Similar results were seen using a 0.35 mm lead equivalent radio-protective film. However, this material adds considerable weight to the surgical drape.

We claim:

1. A method for shielding an operator from radiation during a coronary intervention procedure of a patient with X-ray imaging comprising spreading a sterile surgical drape over the patient to provide shielding,
    wherein the sterile surgical drape comprises an integrated radio-protective layer that does not move independently from the sterile surgical drape and that does not lie in the path of the primary X-ray beam during the coronary intervention procedure,
    wherein the sterile surgical drape is at least 130 cm in width and at least 130 cm in length,
    wherein the integrated radio-protective layer is at least 130 cm in width, and
    wherein the integrated radio-protective layer is at least 60 cm in length,
    wherein the integrated radio-protective layer comprises at least one precut hole that can be opened to allow access to the patient; and
    performing the coronary intervention procedure with X-ray imaging,
    wherein the sterile surgical drape reduces the cumulative dose of the operator of the coronary intervention procedure to 0-5 µSv when accessed through the right radial artery.

2. The method of claim 1, wherein the integrated radio-protective layer has at least two precut holes that can be opened to allow access to the patient.

3. The method of claim 2, wherein the integrated radio-protective layer comprises at least two precut holes of at least 5 cm in diameter and separated by between 90 cm and 110 cm.

4. The method of claim 2, wherein the integrated radio-protective layer comprises at least two precut holes of at least 5 cm in diameter and separated by between 20 cm and 50 cm.

5. The method of claim 2, wherein the integrated radio-protective layer comprises at least two precut holes of at least 5 cm in diameter and separated by between 50 cm and 90 cm.

6. The method of claim 2, wherein the integrated radio-protective layer comprises at least two precut holes of at least 5 cm in diameter and separated by between 90 cm and 110 cm and at least two additional precut holes of at least 5 cm in diameter and separated by between 20 cm and 50 cm.

7. The method of claim 2, wherein the precut holes are between 5 cm and 15 cm in diameter.

8. The method of claim 2, further comprising at least two rectangular extensions of the precut holes of at least 5 cm by 10 cm.

9. The method of claim 1, wherein the integrated radio-protective layer comprises a hole of at least 30 cm×30 cm for passage of the primary X-ray beam.

10. The method of claim 9, wherein the hole is between 30 cm×30 cm and 40 cm×50 cm.

11. The method of claim 1, wherein the surgical drape is at least 190 cm in length.

12. The method of claim 11, wherein the surgical drape is at least 250 cm in length.

13. The method of claim 12, wherein the surgical drape is at least 200 cm in width.

14. The method of claim 1, wherein the integrated radio-protective layer has at least 0.25 mm lead equivalence at 70 kVp.

15. The method of claim 1, wherein the sterile surgical drape reduces the cumulative dose of the operator of the coronary intervention procedure accessed through the right radial artery to 0-4 µSv.

16. The method of claim 1, wherein the sterile surgical drape reduces the cumulative dose of the operator of the coronary intervention procedure accessed through the right radial artery to less than 5 µSv.

17. The method of claim 1, wherein the sterile surgical drape reduces the cumulative dose of the operator of the coronary intervention procedure accessed through the right radial artery to 0-2 µSv.

18. The method of claim 1, wherein the sterile surgical drape reduces the cumulative dose of the operator of the coronary intervention procedure accessed through the right radial artery such that no cumulative dose of the operator is detected.

19. The method of claim 1, wherein the sterile surgical drape reduces the cumulative dose of an assistant of the coronary intervention procedure accessed through the right radial artery such that no cumulative dose of the assistant is detected.

\* \* \* \* \*